United States Patent [19]

Fischer

[11] Plant 5,185

[45] Jan. 31, 1984

[54] AFRICAN VIOLET PLANT

[75] Inventor: Arnold Fischer, Hanover, Fed. Rep. of Germany

[73] Assignee: Pan American Plant Company, Parrish, Fla.

[21] Appl. No.: 390,633

[22] Filed: Jun. 21, 1982

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet cultivar known by the cultivar name Guenevere having profuse red-purple flowers, forming a massive bouquet positioned above symmetrical foliage and carried on erect peduncles.

3 Drawing Figures

The present invention comprises a new and distinct cultivar of African violet plant, botanically known as *Saintpaulia hybrids,* and hereinafter referred to by the cultivar name Guenevere.

The new cultivar was referred to during the breeding and selection process by the designation V7-C43-F, and is a product of a planned breeding program. The basic objective of the breeding program was to create a new African violet cultivar which flowers in 10–12 weeks, and wherein a mass of medium to large red-purple flowers are positioned above medium-sized and symmetrical foliage.

The new cultivar was originated by applicant in 1976 from a cross made in a controlled breeding program in Hannover, West Germany. Both the female and male parents of the new cultivar are unknown at this time.

Guenevere was discovered and selected by me as a flowering plant within the progeny of the stated cross in a controlled environment in Fallbrook, Calif. Asexual reproduction of the new cultivar by leaf cuttings, as performed by me at Fallbrook, Calif., has demonstrated that the combination of characteristics as herein disclosed for the new cultivar are firmly fixed and are retained through successive generations of asexual reproduction.

Guenevere has not been observed under all possible environmental conditions. The phenotype may vary significantly with variations in environment such as temperature, light intensity and day length. The following observations, measurements and values describe the new cultivar as grown in Fallbrook, Calif. and Parrish, Fla., under greenhouse conditions which closely approximate those generally used in commercial practice.

The following traits have been repeatedly observed and are determined to be the basic characteristics of Guenevere, which in combination distinguish this African violet as a new and distinct cultivar:

1. A profusion of medium-size red-purple flowers positioned in a massive bouquet well above the generally medium green foliage.
2. The flowers are carried on erect peduncles.
3. The plant may be finished from a $2\frac{1}{4}''$ plant to essentially full growth in approximately 10–12 weeks in a controlled environment.
4. The medium-sized and symmetrical foliage provides a pleasant contrast with the massive flower bouquet positioned above the foliage.

The accompanying photographic drawings show a typical specimen plant of the new cultivar, and its components. Sheet 1 comprises a color photograph showing principally the flower bouquet in perspective view, and a second photograph showing individual blooms and an adjacent color chart from which the accuracy of the below stated color values will be evident. The colors appearing in the photograph are as true as possible with color illustrations of this type. Sheet 2 comprises four separate views of foliage at various stages of growth or positioning on the plant, taken from the underside.

In the following description, color references are made to The Royal Horticultural Society Color Chart (RHS), except where general colors of ordinary significance are referred to. Color values were taken under indirect natural light conditions.

Botanical classification: *Saintpaulia hybrids,* cv. Guenevere.

Parentage:

*Male parent.*—Unknown.

*Female parent.*—Unknown.

Propagation: The new cultivar holds its distinguishing characteristics through successive propagations by leaf cuttings.

Plant: From 8 cm. to 12 cm. tall when grown in pots, with the growth rate being normal and the plant having a rounded-rosette shape.

*Leaves.*—General form: Oval with broadly acute apex and cordate base, with repand margins. The leaves are profuse. Diameter: 4×5 cm. to 7×8 cm. Texture: Glossy. Veins: Pinnate. Color (Upperside): 147A. Color (Underside): 147D. Petiole: 6–11 cm. in length.

*Flowers.*—Buds: Approximately 1 cm. in length and diameter, and rounded in shape. Rate of opening normal for African violets. Color: When sepals first divide, 78D; when petals begin to unfurl, 72B. Sepals: Shape: Lanceolate, 5 in number, with the sepals standing up when flowers open. Color: Inside, 148B, outside, 148B. Phyllaries: Shape: Lanceolate, 2 in number. Color: 177B. Peduncles: 2–4 cm. in length at bud stage, hairy, erect, and slender, color 177B. Calyx: Relatively small, funnel-shaped, splits, hairy.

*Individual flowers.*—Size: Medium, 3–4 cm. in diameter, 5 petals. Shape: Generally cup-shaped when blooms first open, expanding to slightly cup-shaped as blooms mature; flowers appear in clusters, with petals being sympetalously arranged, single zygomorphic, margin entire, and apex rounded. Color: Upperside: Approximately 72B, taken in February under indirect natural light. Underside: 72A. Borne: On upright peduncles having normal strength and being 6–10 cm. in length when fully grown, color 177B; profuse flowering. Texture: Soft, with a satiny appearance. Flowering Habit: Blooms profusely and intermittently year round, with petals drying up as opposed to dropping. Blooms last approximately 2–3 weeks.

Reproductive organs:

*Stamens.*—2 in number, borne singly to one side of ovary, anthers basifixed. Anthers: 2 mm.$^2$, yellow in color. Filaments: 2–3 mm. in length.

*Pistels.*—1 in number. Styles: 5–6 mm. in length, color 72B. Pollen color: Yellow. Ovaries: Superior.

Disease resistance: No disease problems noted to date.

General observations: Guenevere is a profuse flowering cultivar having red-purple flowers borne on erect peduncles in a massive bouquet above the medium-green, symmetrical foliage, thereby providing a highly attractive flowering plant.

I claim:

1. A new and distinct cultivar of African violet known by the cultivar name Guenevere, as described and illustrated, and particularly characterized by its profuse flowering, red-purple flower color, erect and relatively long peduncles which elevate the profuse bouquet above the medium-size and symmetrical foliage, and by its 10–12 weeks flowering time.

* * * * *

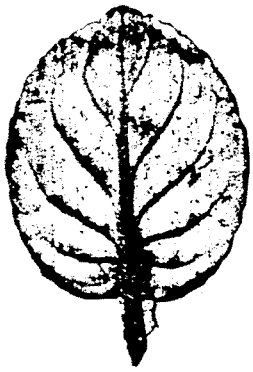
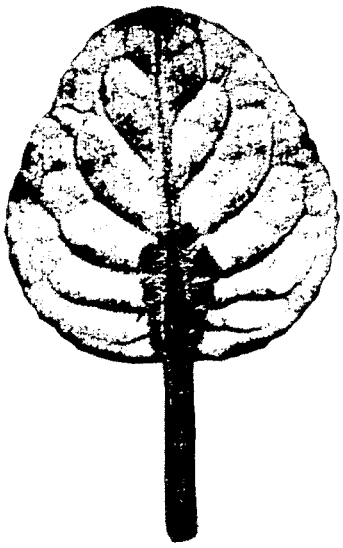
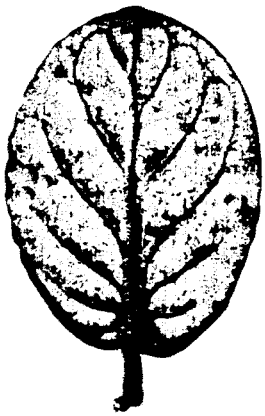
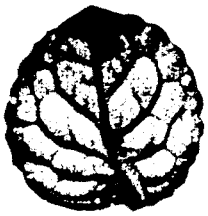

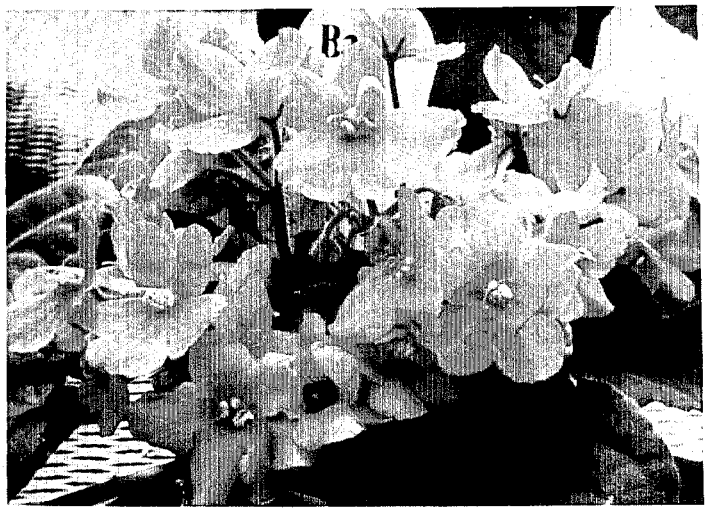
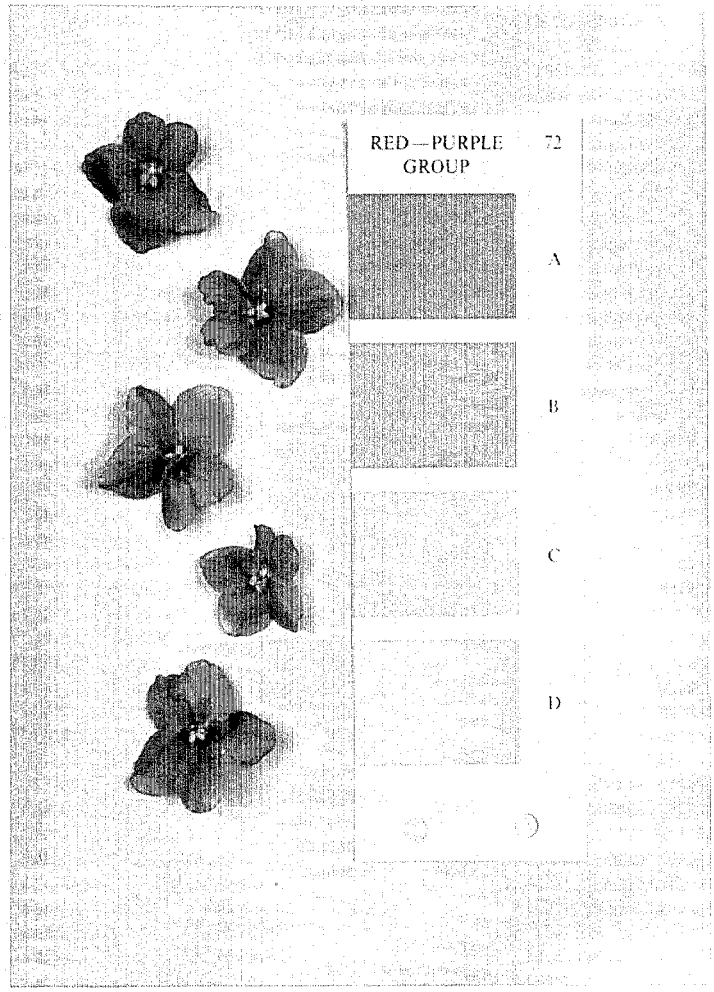
RED—PURPLE GROUP
72
A
B
C
D